(12) United States Patent
Michal et al.

(10) Patent No.: US 8,187,621 B2
(45) Date of Patent: *May 29, 2012

(54) METHODS AND COMPOSITIONS FOR TREATING POST-MYOCARDIAL INFARCTION DAMAGE

(75) Inventors: Eugene Michal, San Francisco, CA (US); Shubhayu Basu, Mountain View, CA (US); Hai-Chien Kuo, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1367 days.

This patent is subject to a terminal disclaimer.

(21) Appl. No.: 11/447,340

(22) Filed: Jun. 5, 2006

(65) Prior Publication Data

US 2007/0218118 A1    Sep. 20, 2007

Related U.S. Application Data

(63) Continuation-in-part of application No. 11/361,920, filed on Feb. 23, 2006, which is a continuation-in-part of application No. 11/110,223, filed on Apr. 19, 2005.

(51) Int. Cl.
*A61K 9/127* (2006.01)
*A61P 7/00* (2006.01)

(52) U.S. Cl. .................. 424/423; 424/450; 424/491

(58) Field of Classification Search .................. None
See application file for complete search history.

(56) References Cited

U.S. PATENT DOCUMENTS

| | | |
|---|---|---|
| 3,780,733 A | 12/1973 | Martinez-Mangor |
| 4,141,973 A | 2/1979 | Balazs |
| 4,617,186 A | 10/1986 | Schafer |
| 4,794,931 A | 1/1989 | Yock |
| 4,818,291 A | 4/1989 | Iwatsuki et al. |
| 5,000,185 A | 3/1991 | Yock |
| 5,024,234 A | 6/1991 | Leary et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Siepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,642,234 A | 6/1997 | Altman et al. |
| 5,655,548 A | 8/1997 | Nelson et al. |
| 5,667,778 A | 9/1997 | Atala |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,740,808 A | 4/1998 | Panescu et al. |
| 5,749,915 A | 5/1998 | Slepian |
| 5,785,689 A | 7/1998 | De Toledo et al. |
| 5,810,885 A | 9/1998 | Zinger |

(Continued)

FOREIGN PATENT DOCUMENTS

EP    0331584    9/1989

(Continued)

OTHER PUBLICATIONS

PCT International Preliminary Report on Patentability and Written Opinion dated Dec. 24, 2008 for PCT/US2007/013181, 11 pages.
Abbott Cardiovascular Systems in, PCT Search Report and Written Opinion dated Aug. 26, 2008 for PCT/US2007/016433.
Abbott Cardiovascular Systems in, PCT Search Report and Written Opinion dated Jul. 31, 2008 for PCT/US2007/024158.
Advanced Cardiovascular Systems, Inc. et al., PCT International Preliminary Report on Patentability dated Jun. 19, 2007, PCT Appln. No. PCT/US2005/045627.
Advanced Cardiovascular Systems, Inc., PCT Search Report and Written Opinion dated Nov. 24, 2004, PCT Appln. No. PCT/US2004/011356, 12 pages.

(Continued)

*Primary Examiner* — Lisa J Hobbs

(74) *Attorney, Agent, or Firm* — Randy Shen; Blakely Sokoloff Taylor & Zafman LLP

(57) ABSTRACT

Methods and compositions for treating post-myocardial infarction damage are herein disclosed. In some embodiments, a carrier with a treatment agent may be fabricated. The carrier can be formulated from a bioerodable, sustained-release substance. The resultant loaded carrier may then be suspended in at least one component of a two-component matrix system for simultaneous delivery to a post-myocardial infarction treatment area.

13 Claims, 7 Drawing Sheets

U.S. PATENT DOCUMENTS

| | | | |
|---|---|---|---|
| 5,811,533 A | 9/1998 | Gold et al. |
| 5,827,313 A | 10/1998 | Ream |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon et al. |
| 5,979,449 A | 11/1999 | Steer |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,151,525 A | 11/2000 | Soykan et al. |
| 6,152,141 A | 11/2000 | Stevens et al. |
| 6,153,428 A | 11/2000 | Gustafsson et al. |
| 6,159,443 A | 12/2000 | Hallahan |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | VanTassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 * | 3/2002 | Ley et al. ............... 607/127 |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,432,119 B1 | 8/2002 | Saadat |
| 6,436,135 B1 | 8/2002 | Goldfarb |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett |
| 6,465,001 B1 | 10/2002 | Hubbell et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,548,081 B2 | 4/2003 | Sadozai et al. |
| 6,554,801 B1 | 4/2003 | Steward et al. |
| 6,599,267 B1 | 7/2003 | Ray et al. |
| 6,602,241 B2 | 8/2003 | Makower et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,231 B1 | 8/2004 | Katz et al. |
| 6,790,455 B2 | 9/2004 | Chu et al. |
| 6,858,229 B1 | 2/2005 | Hubbell et al. |
| 6,916,648 B2 | 7/2005 | Goddard et al. |
| 6,992,172 B1 * | 1/2006 | Chang et al. ............... 530/354 |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,273,469 B1 | 9/2007 | Chan et al. |
| 7,374,774 B2 * | 5/2008 | Bowlin et al. ............... 424/423 |
| 7,615,373 B2 * | 11/2009 | Simpson et al. ............... 435/398 |
| 7,815,590 B2 | 10/2010 | Cooper |
| 2001/0023349 A1 | 9/2001 | VanTassel et al. |
| 2001/0055615 A1 | 12/2001 | Wallace et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0090725 A1 * | 7/2002 | Simpson et al. ............... 435/402 |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |

| | | | |
|---|---|---|---|
| 2003/0175410 | A1* | 9/2003 | Campbell et al. ............ 427/2.24 |
| 2004/0002650 | A1 | 1/2004 | Mandrusov et al. |
| 2004/0181206 | A1 | 9/2004 | Chiu |
| 2004/0185084 | A1 | 9/2004 | Rhee et al. |
| 2004/0208845 | A1 | 10/2004 | Michal et al. |
| 2004/0213756 | A1 | 10/2004 | Michal et al. |
| 2005/0015048 | A1 | 1/2005 | Chiu |
| 2005/0031874 | A1 | 2/2005 | Michal et al. |
| 2005/0042254 | A1 | 2/2005 | Freyman et al. |
| 2005/0065281 | A1 | 3/2005 | Lutolf et al. |
| 2005/0070844 | A1 | 3/2005 | Chow |
| 2005/0186240 | A1 | 8/2005 | Ringeisen et al. |
| 2005/0281883 | A1 | 12/2005 | Daniloff et al. |
| 2006/0149392 | A1 | 7/2006 | Hsieh et al. |
| 2006/0233850 | A1 | 10/2006 | Michal |
| 2007/0270948 | A1 | 11/2007 | Wuh |
| 2008/0025943 | A1 | 1/2008 | Michal et al. |

FOREIGN PATENT DOCUMENTS

| | | |
|---|---|---|
| EP | 0861632 A1 | 9/1998 |
| EP | 0938871 A2 | 9/1999 |
| GB | 2194144 A1 | 3/1988 |
| JP | 61205446 | 9/1986 |
| JP | 2003062089 | 3/2003 |
| WO | WO 92/10142 A1 | 6/1992 |
| WO | WO 98/30207 | 7/1998 |
| WO | WO 98/54301 A2 | 12/1998 |
| WO | WO-9953943 | 10/1999 |
| WO | WO 00/16818 | 3/2000 |
| WO | WO-0054661 | 9/2000 |
| WO | WO 00/71196 A1 | 11/2000 |
| WO | WO 01/24775 A1 | 4/2001 |
| WO | WO-0124842 | 4/2001 |
| WO | WO 01/45548 A2 | 6/2001 |
| WO | WO 01/49357 A2 | 7/2001 |
| WO | WO-0200173 | 1/2002 |
| WO | WO-0204008 | 1/2002 |
| WO | WO 02/28450 A2 | 4/2002 |
| WO | WO 02/40070 A2 | 5/2002 |
| WO | WO-02/072166 | 9/2002 |
| WO | WO 02/087623 A1 | 11/2002 |
| WO | WO-03/022909 | 3/2003 |
| WO | WO 03/027234 A2 | 4/2003 |
| WO | WO-03026492 | 4/2003 |
| WO | WO 03/064637 A1 | 8/2003 |
| WO | WO-2004/000915 | 12/2003 |
| WO | WO 2004/050013 A2 | 6/2004 |
| WO | WO 2004/066829 A2 | 8/2004 |
| WO | WO 2004/091592 | 10/2004 |
| WO | WO 2004/091592 A2 | 10/2004 |
| WO | WO 2005/061019 | 7/2005 |
| WO | WO 2005/067890 | 7/2005 |
| WO | WO 2006/039704 | 4/2006 |
| WO | WO 2006/113407 | 10/2006 |
| WO | WO 2007/048831 | 3/2007 |
| WO | WO-2007145909 | 12/2007 |

OTHER PUBLICATIONS

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, Jan. 1995, pp. 284-288.

Haugland, et al., "Dialkylcarbocyanine and Dialkylaminostryryl Probes", Handbook of Fluorescent Probes and Research Products, Molecular Probes, Inc., 2002, pp. 530-534.

Haugland, et al., "Membrane-permeant reactive tracers", Handbook of Fluorescent Probes and Research Products, Molecular Probes, Inc., 2002, pp. 458-553.

Hoffman, "Hydrogels for Biomedical Applications", Advanced Drug Delivery Reviews, vol. 43, 2002, pp. 3-12.

Horan, R.L., et al., "In Vitro Degradation of Silk Fibroin", Biomaterials, vol. 26, 2004, pp. 3385-3393.

Kaplan, D.L., et al., "Spiderless Spider Webs", Nature Biotechnology, vol. 20, 2002, pp. 239-240.

Kim, Ung-Jin, et al., "Structure and Properties of Silk Hydrogels", Biomacromolecules, vol. 5(3), 2004, pp. 786-792.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, Jan. 2001, pp. 1848-1853.

Meinel, L., et al., "The Inflammatory Responses to Silk Films In Vitro and In Vivo", Biomaterials, vol. 26, 2005, pp. 147-155.

Nazarov, R., et al., "Porous 3-D Scaffolds from Regenerated Silk Fibroin", Biomacromolecules, vol. 5(3), 2004, pp. 718-726.

Nikolic, Serjan D., et al., "Novel means to improve coronary blood flow", Clinical Science, Abstracts from Scientific Sessions, 2000, pp. II-689.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, Dec. 1986, pp. 2649-2658.

Wang, M., et al., "Mechanical Properties of Electrospun Silk Fibers", Macromolecules, vol. 37(18), 2004, pp. 6856-6864.

Wilensky, R., et al., "Direct intraarterial wall injection of microparticles via a catheter: a potential durg delivery strategy following angioplasty", American Heart Journal, 122, 1991, pp. 1136.

Yager, P., et al., "Silk Protein Project", www.faculty.washington.edu/yagerp/silkprojecthome.html, Aug. 23, 199), 18 pages.

Yeo, L.Y., et al., "AC Electrospray Biomaterials Synthesis", Biomaterials, 2005, 7 pages.

Abbott Cardiovascular Systems Inc, PCT International Search Report and Written Opinion mailed Feb. 10, 2009 for PCT Application No. PCT/US2007/023419, 17 pages.

Friedman, Paul M. et al., "Safety Data of Injectable Nonanimal Stabilized Hyaluronic Acid Gel for Soft Tissue Augmentation," Dermatologic Surgery, 2002, vol. 28, pp. 491-494.

Choi, et al., "Study on gelatin-containing artificial skin: I. Preparation and characteristics of novel gelatin-alginate sponge," Biomaterials, 1999, vol. 20, pp. 409-417.

Dong, et al., "Alginate/gelatin blend films and their properties for drug controlled release," Journal of Membrane Science, 2006, vol. 280, pp. 37-44.

Lutolf, et al., "Synthesis and Physicochemical Characterization of End-Linked Poly(ethylene glycol)-co-peptide Hydrogels Formed by Michael-Type Addition," Biomacromolecules, 2003, vol. 4, pp. 713-722.

Segura, et al., "DNA delivery from hyaluronic acid-collagen hydrogels via a substrate-mediated approach," Biomaterials, 2005, vol. 26, pp. 1575-1584.

Shu, et al., "In situ crosslinkable hyaluronan hydrogels for tissue engineering," Biomaterials, 2004, vol. 25, pp. 1339-1348.

PCT Search Report for PCT Appln No. PCT/US2006/014021, mailed Jan. 31, 2007 (11 pages).

PCT Search Report for PCT Appln No. PCT/US2007/013181, mailed Feb. 12, 2008 (17 pages).

PCT Search Report for PCT Appln No. PCT/US2007/003614, mailed Mar. 27, 2008 (18 pages).

Khademhosseini, et al., "Microscale Technologies for Tissue Engineering and Biology", PNAS, Feb. 21, 2006, vol. 103, No. 8, pp. 2480-2487.

Kelly, E.B., "Advances in Mammalian and Stem Cell Cloning", Genetic Engineering News, vol. 23, No. 7, Apr. 1, 2003, pp. 17-18 & 68.

Li, et al., "Cell Therapy to Repair Broken Hearts", Can. J. Cardiol, vol. 14, No. 5, May 1998, pp. 735-744.

Leibovich, S.J., et al., "Macrophage-Induced Angiogenesis is Mediated by Tumour Necrosis Factor-α.", Nature, vol. 329, Oct. 15, 1987, pp. 630-632.

De Rosa, et al., "Biodegradable Microparticles for the Controlled Delivery of Oligonucleotides", International Journal of Pharmaceutics, Aug. 21, 2002, 242: pp. 225-228.

Abbott Cardiovascular Systems, Office Action dated Mar. 30, 2009 for U.S. Appl. No. 10/792,960.

Abbott Cardiovascular Systems, Office Action dated Apr. 13, 2009 for U.S. Appl. No. 11/566,643.

Abbott Cardiovascular Systems, Office Action dated Apr. 29, 2009 for U.S. Appl. No. 12/013,286.

Abbott Cardiovascular Systems, Office Action dated May 12, 2009 for U.S. Appl. No. 11/496,824.

Abbott Cardiovascular Systems, Non-Final Office Action dated Mar. 13, 2009 for U.S. Appl. No. 10/414,602.

Elbert, D. L., et al., "Protein delivery from materials formed by self-selective conjugate addition reactions", Journal of Controlled Release, 76, (2001), 11-25.

Staatz, WD, et al., "Identification of a tetrapeptide recognition sequence for the alpha 2 beta 1 integrin in collagen", Journal of Biological Chemistry, 1991, 266(12), pp. 7363-7367.

Abbott Cardiovascular Systems, International Preliminary Report on Patentability dated Jul. 30, 2009 for PCT/US2008/051505.

Abbott Cardiovascular Systems, Final office action dated Nov. 12, 2009 for U.S. Appl. No. 12/013,286.

Abbott Cardiovascular Systems, Final office action dated Nov. 25, 2009 for U.S. Appl. No. 11/566,643.

Abbott Cardiovascular Systems, Non final office action dated Dec. 9, 2009 for U.S. Appl. No. 10/781,984.

Abbott Cardiovascular Systems, Examination Report dated Jan. 13, 2010 for EP Application No. 07795729.8.

Abbott Cardiovascular Systems, Final Office Action dated Jan. 29, 2010 for U.S. Appl. No. 10/792,960.

Abbott Cardiovascular Systems, Examination Report dated Jan. 15, 2010 for EP 08727952.7.

Abbott Cardiovascular Systems, Examination Report dated Feb. 5, 2010 for EP 07810637.4.

Abbott Cardiovascular Systems, International search report and written opinion dated Jun. 18, 2009 for PCT/US2008/051505.

Abbott Cardiovascular Systems, Non final office action dated Jul. 9, 2009 for U.S. Appl. No. 11/561,328.

Abbott Cardiovascular Systems, Non final office action dated Apr. 14, 2010 for U.S. Appl. No. 12/016,180.

Abbott Cardiovascular Systems, Final office action dated Apr. 22, 2010 for U.S. Appl. No. 10/414,602.

Abbott Cardiovascular Systems, Non final office action dated Apr. 29, 2010 for U.S. Appl. No. 10/792,960.

Abbott Cardiovascular Systems, Non-Final Office Action dated Jun. 4, 2010 for U.S. Appl. No. 10/781,984.

Abbott Cardiovascular Systems, Final Office Action Mailed Jun. 11, 2010 for U.S. Appl. No. 11/561,328.

Hao, X, et al., "Angiogenic effects of sequential release of VEGF-A165 and PDGF-BB with alginate hydrogels after myocardial infarction", Cardiovascular Research, 75, (2007), 178-185.

Ritter, A. B., et al., "Elastic modulus, distensibility, and compliance (capacitance)", Biomedical Engineering Principles, Chapter 4, (2005), 187-191.

Zheng, Shu, et al., "In situ crosslinkable hyaluronan hydrogels for tissue engineering", Biomaterials, Elsevier Science Publishers, vol. 25, No. 7-8, (2004), 1339-1348.

Abbott Cardiovascular Systems, Final office action mailed Sep. 27, 2010 for U.S. Appl. No. 10/792,960.

Abbott Cardiovascular Systems, Final office action mailed Sep. 27, 2010 for U.S. Appl. No. 12/016,180.

Abbott Cardiovascular Systems, Final Office Action mailed Nov. 22, 2010 for U.S. Appl. No. 10/781,984, 13 pages.

Abbott Cardiovascular Systems, Non-final Office Action mailed Nov. 24, 2010 for U.S. Appl. No. 12/013,286, 11 pages.

Abbott Cardiovascular Systems, Non-final Office Action mailed Dec. 8, 2010 for U.S. Appl. No. 11/566,643, 17 pages.

Abbott Cardiovascular Systems, Non-final Office Action mailed Dec. 10, 2010 for U.S. Appl. No. 11/938,752, 32 pages.

Abbott Cardiovascular Systems, Non-final Office Action mailed Dec. 17, 2010 for U.S. Appl. No. 11/933,922, 23 pages.

Abbott Cardiovascular Systems, website for Healon (R) OVD, copyright 2010, accessed Dec. 15, 2010, URL: <http://abbottmedicaloptics.com/products/cataract/ovds/healon-viscoelastic>, (2010), 2 pages.

Abbott Cardiovascular Systems, *Product Information Sheet for Healon (R), from Abbott Medical Abbott Optics*, (2005), 1 page.

Abbott Cardiovascular Systems, Japanese Office Action dated Dec. 8, 2010 for Japanese Patent App No. 2006-509975., 6 pages.

Abbott Cardiovascular Systems, Non final office action mailed Feb. 8, 2011 for U.S. Appl. No. 10/792,960.

Haynesworth, Stephen E., et al., "Platelet Effects on Human Mesenchymal Stem Cells", Abstract, *presented at Orthopaedic Research Society 48th Annual Meeting*, Dallas, TX (Feb. 10-13, 2010), 2 pages.

Abbott Cardiovascular Systems, Final Office Action mailed Apr. 15, 2011 for U.S. Appl. No. 10/414,602.

Advanced Cardiovascular Systems, Extended European search report dated Apr. 21, 2011 for EP Application No. 10186186.2.

Advanced Cardiovascular Systems, Extended EP Search Report dated May 20, 2011 for EP Application No. 10186197.9.

Chung, Y., et al., "Sol-gel transition temperature of PLGA-g-PEG aqueous solutions", Biomacromolecules, vol. 3, No. 3, (May 2002), 511-516.

Abbott Cardiovascular Systems, Non final office action mailed Jul. 6, 2011 for U.S. Appl. No. 10/781,984.

Abbott Cardiovascular Systems, Final office action mailed Jun. 28, 2011 for U.S. Appl. No. 10/792,960.

Abbott Cardiovascular Systems, Final office action mailed Jul. 18, 2011 for U.S. Appl. No. 11/566,643.

Abbott Cardiovascular Systems Non-Final Office Action mailed Aug. 31, 2011 for U.S. Appl. No. 11/110,223.

Abbott Cardiovascular Systems, Final office action mailed Sep. 20, 2011 for U.S. Appl. No. 11/938,752.

Agocha A. et al. "Hypoxia regulates basal and induced DNA synthesis and collagen type I production in human cardiac fibroblasts: effects of transforming growth factor-beta 1, thyroid hormone, angiotensin II and basic fibroblast growth factor," *J. Mol. Cell. Cardiol.* 29(8): 2233-2244. (Apr. 1997).

Allemann, E. et al. "Kinetics of Blood Component Adsorption on poly(D,L-lactic acid) Nanoparticles: Evidence of Complement C3 Component Involvement," *J. Biomed. Mater Res.* 37(2):229-234 (Nov. 1997), Abstract downloaded from the Internet at: http://www.ncbi.nlm.nih.gov/entrez/query.fcgi?cmd=Retrieve%db=PubMed, 1 page.

Anderson, J. et al. "Biodegradation and Biocompatibility of PLA and PLGA Microspheres," *Advanced Drug Delivery Reviews* 28 (1997), pp. 5-24.

Assmus, B. et al. "Transplantation of Progenitor Cells and Regeneration Enhancement in Acute Myocardial Infarction (Topcare-AMI)," *Circulation* (2002), 106:3009-3017, first page only (1 page).

Baxter, "FloSeal Matrix Hemostatic Sealant," downloaded from the Internet on Nov. 14, 2002, from: http://www.fusionmed.com/docs/surgeon/default.asp, 2 pages.

Berger et al. "Poly-L-cysteine," *J. Am. Chem. Soc.* 78(17):4483-4488 (Sep. 5, 1956).

Bernatowicz, M. et al. "Preparation of Boc-[S-(3-nitro-2-pyridinesulfenyl)]-cysteine and its use for Unsymmetrical Disulfide Bond Formation," *Int. J. Peptide Protein Res.* 28(2):107-112 (Aug. 1996).

Boland, E.D. "Electrospinning Collagen and Elastin: Preliminary Vascular Tissue Engineering," *Frontiers in Bioscience* vol. 9, pp. 1422-1432 (May 1, 2004).

Brust, G. "Polyimides," downloaded from the Internet at: http://www.pslc.ws/macrog/imide.htm, 4 pages (© 2005).

Buschmann, I. et al. "Arteriogenesis Versus Angiogenesis: Two Mechanisms of Vessel Growth," *News Physiol. Sci.* vol. 14 (Jun. 1999), pp. 121-125.

Canderm Pharma, "Technical Dossier: Artecoll," downloaded from the Internet on Oct. 22, 2002 from: http://www.canderm.com/artecoll/tech.html, 3 pages.

Capan, Y. et al. "Preparation and Characterization of Poly(D,L-lactide-co-glycolide) Microspheres for Controlled Release of Human Growth Hormone," *AAPS PharmSciTech.* 2003; 4(2): article 28. Downloaded from the Internet at: http://www.aapspharmscitech.org/view.asp?art=pt040228&pdf=yes (12 pages).

Caplan, M.J. et al. "Dependence on pH of Polarized Sorting of Secreted Proteins," *Nature* 329 (Oct. 15, 1987), p. 630.

Carpino, L. et al. "Tris(2-aminoethyl)amine as a Substitute for 4-(Aminomethyl)piperidine in the FMOC/Polyamine Approach to Rapid Peptide Synthesis," *J. Org. Chem.* 55(5):1673-1675 (Mar. 1990).

Chandy et al. "The Development of Porous Alginate/Elastin/PEG Composite Matrix for Cardiovascular Engineering," *Journal of Biomaterials Applications*, vol. 17 (Apr. 2003), pp. 287-301.

Corbett, S. et al. "Covalent Cross-linking of Fibronectin to Fibrin is Required for Maximal Cell Adhesion to a Fibronectin-Fibrin Matrix," *The Journal of Biological Chemistry*, 272(40):24999-25005 (Oct. 3, 1997).

Creemers, E. et al. "Matrix Metalloproteinase Inhibition After Myocardial Infarction: A New Approach to Prevent Heart Failure?" *Circ. Res.* vol. 89:201-210 (2001).

Crivello, et al. "Synthesis and Photoinitiated Cationic Polymerization of Monomers with the Silsesquioxane Core," *J Polym Science: Part A: Polymer Chemistry* 35:407-425 (1997).

Davis, M.E. et al., "Injectable Self-Assembling Peptide Nanofibers Create Intramyocardial Microenvironments for Endothelial Cells" *Circulation* 111:442-450 (Feb. 2005).

Desai, M. et al. "Polymer bound EDC (P-EDC): A convenient reagent for formation of an amide bond," *Tetrahedron Letters* 34(48):7685-7688 (Nov. 1993), Abstract downloaded from the Internet at: http://www.sciencedirect.com, 1 page.

Dinbergs et al. "Cellular Response to Transforming Growth Factor-β1 and Basic Fibroblast Growth Factor Depends on Release Kinetics & Extracellular Matrix Interactions," *J. Bio Chem* 271(47):29822-29829 (Nov. 22, 1996).

Edelman, E.R. et al. "Controlled & Modulated Release of Basic Fibroblast Growth Factor," *Biomaterials* vol. 12 (Sep. 1991), pp. 619-626.

Etzion, Sharon et al. "Influence of Embryonic Cardiomyocyte Transplantation on the Progression of Heart Failure in a Rat Model of Extensive Myocardial Infarction," *J. Mol. Cell Cardiol.* 33:1321-1330 (May 2001).

Ferrara, N. "Role of Vascular Endothelial Growth Factor in the Regulation of Angiogenesis," *Kidney International* 56(3):794-814 (1999), Abstract downloaded from the Internet at: http://www.nature.com/ki/journal/v56/n3/abs/4490967a.html, 1 page.

Fuchs, S. et al. "Catheter-Based Autologous Bone Marrow Myocardial Injection in No-Option Patients with Advanced Coronary Artery Disease," *J. Am. Coll. Cardiol.* 41(10):1721-1724 (2003).

Fukumoto, S. et al. "Protein Kinase C δ Inhibits the Proliferation of Vascular Smooth Muscle Cells by Suppressing $G_1$ Cyclin Expression," The Journal of Biological Chemistry 272(21):13816-13822 (May 1997).

Giordano, F. et al. "Angiogenesis: The Role of the Microenvironment in Flipping the Switch," *Current Opinion in Genetics and Development* (2001), 11:35-40.

Gossler, et al. "Transgenesis by means of blastocyst-derived embryonic stem cell lines," *Proc. Natl. Acad. Sci. USA*, 83:9065-9069 (Dec. 1986).

Grafe, T.H., "Nanofiber Webs from Electrospinning" Presented at the *Nonwovens in Filtration—Fifth International Conference*, Stuttgart, Germany, Mar. 2003, pp. 1-5.

Gref, R. et al. "Biodegradable Long-Circulating Polymeric Nanospheres," *Science* 263(5153):1600-1603 (Mar. 1994), Abstract downloaded from the Internet at: http://www.sciencemag.org/cgi/content/abstract/263/5153/1600, 1 page.

Grund, F. et al. "Microembolization in Pigs: Effects on Coronary Blood Flow and Myocardial Ischemic Tolerance," *AM J. Physiol.* 277 (*Heart Circ. Physiol. 46*):H533-H542 (1999).

Gupta et al. "Changes in Passive Mechanical Stiffness of Myocardial Tissue with Aneurysm Formation," *Circulation*, 89(5):2315-2326 (May 1994).

Hashimoto, T. et al. "Development of Alginate Wound Dressings Linked with Hybrid Peptides Derived from Laminin and Elastin," *Biomaterials* 25 (2004), pp. 1407-1414.

Heeschen, C. et al. "Nicotine Stimulates Tumor Angiogenesis," *American College of Cardiology* 37(2) Supplement A, pp. 1A-648A (Feb. 2001), Abstract downloaded from the Internet at: http://24.132.160.238/ciw-01acc/abstract_search_author.cfm?SearchName=Heeschen, 1 page.

Helisch, A. et al. "Angiogenesis and Arteriogenesis—Not yet for prescription," Neue Diagnostische Und Therap. Verfahren, *Z. Kardiol.* 89:239-244 Steinkopff Verlag (2000).

Hendel, R.C. et al. "Effect of Intracoronary Recombinant Human Vascular Endothelial Growth Factor on Myocardial Perfusion: Evidence for a Dose-Dependent Effect," *Circulation* 101:118-121 (2000).

Henry, R.R. et al. "Insulin Action and Glucose Metabolism in Nondiabetic Control and NIDDM Subjects. Comparison Using Human Skeletal Muscle Cell Cultures" Diabetes, 44(8):936-946 (1995), Abstract downloaded from the Internet at: http://diabetes.diabetesjournals.org/cgi/content/abstract/44/8/936, 1 page.

Holland, N.B. et al. "Biomimetic Engineering of Non-Adhesive glycocalyx-like Surfaces Using Oligosaccharide Surfactant Polymers," *Nature* 392:799-801 (Apr. 1998), Abstract downloaded from the Internet at: http://www.nature.com, 1 page.

Hovinen, J. et al. "Synthesis of 3'-functionalized oligonucleotides on a single solid support," *Tetrahedron Letters* 34(50):8169-8172 (Dec. 1993), Abstract downloaded from the Internet at: http://www.sciencedirect.com, 1 page.

Huang, K. et al. "Synthesis and Characterization of Self-Assembling Block Copolymers Containing Bioadhesive End Groups," *Biomacromolecules* (2002), 3(2):397-406.

Hutcheson, K. et al. "Comparison of Benefits on Myocardial Performance of Cellular Cardiomyoplasty with Skeletal Myoblasts and Fibroblasts," *Cell Transplantation* (2000), 9(3):359-368.

Huynh, T.V. et al. "Constructing and Screening cDNA Libraries in λgt10 and λgt11," Chapter 2, in *DNA Cloning, vol. 1: A Practical Approach*, ed. By D.M. Glover, pp. 49-78, Jul. 1985.

Indik, Z.. et al. "Production of Recombinant Human Tropoelastin: Characterization and Demonstration of Immunologic and Chemotactic Activity," *Arch. Biochem. Biophys.* 280(1):80-86 (Jul. 1990), Abstract downloaded from the Internet at: http://www.ncbi.nlm.nih.gov/entrez/query.fcgi?cmd=Retrieve&db=PubMed, 1 page.

Iskandrian, A.S. et al. "Nuclear Cardiac Imaging: Principles and Applications," second edition, F.A. Davis Co., Philadelphia (1996), cover page, title page and TOC (5 pages total).

Isner, J.M. "Vascular Endothelial Growth Factor: Gene Therapy and Therapeutic Angiogenesis" *Am. J. Cardiol.* Nov. 19, 1998; 82(10A):63S-64S.

Ito, W. D. et al. "Monocyte Chemotactic Protein-1 Increases Collateral and Peripheral Conductance After Femoral Artery Occlusion," *Circulation Research*, 80(6):829-837, (Jun. 1997).

Johnson, O.L. et al. "The Stabilization & Encapsulation of Human Growth Hormone into Biodegradable Microspheres," *Pharmaceutical Research*, 14(6):730-735 (1997).

Jonasson, P. et al. "Denatured states of human carbonic anhydrase II: an NMR study of hydrogen/deuterium exchange at tryptophan-indole-$H_n$ sites," *FEBS Letters* 445 (1999), pp. 361-365.

Källtorp, M. et al. "Inflammatory Cell Recruitment, Distribution, and Chemiluminescence Response at IgG Precoated- and Thiol Functionalized Gold Surfaces," *J. Biomed. Mater. Res.*, 47:251-259 (1999).

Kawai, K. et al. "Accelerated Tissue Regeneration Through Incorporation of Basic Fibroblast Growth Factor-Impregnated Gelatin Microspheres into Artificial Dermis," *Biomaterials* 21 (2000), pp. 489-499.

Kawasuji, M. et al. "Therapeutic Angiogenesis with Intramyocardial Administration of Basic Fibroblast Growth Factor," *Ann Thorac Surg* 69:1155-1161 (2000), Abstract downloaded from the Internet at: http://ats.ctsnetjournals.org/cgi/content/abstract/69/4/115, 2 pages.

Kelley et al. "Restraining Infarct Expansion Preserves Left Ventricular Geometry and Function After Acute Anteroapical Infarction," Circulation (1999), 99:135-142.

Kim, D. et al. "Glow Discharge Plasma Deposition (GDPD) Technique for the Local Controlled Delivery of Hirudin from Biomaterials," *Pharmaceutical Research* (1998), 15( 5):783-786.

Kinart et al. "Electrochemical Studies of 2-hydroxy-3-(3,4-dimethyl-9-oxo-9H-thioxanthen-2-yloxy)N,N,N-trimethyl-1-propanium chloride," *J. Electroanal. Chem* 294 (1990), pp. 293-297.

Kipshidze, N. et al. "Therapeutic Angiogenesis for Critical Limb Ischemia to Limit or Avoid Amputation," *The Journal of Invasive Cardiology* 11(1):25-28, (Jan. 1999).

Klein, S. et al. "Fibroblast Growth Factors as Angiogenesis Factors: New Insights Into Their Mechanism of Action," in *Regulation of Angiogenesis*, I.D. Goldberg and E.M. Rosen (eds.), 1997; 79:159-192.

Klugherz, B. et al. "Gene Delivery From a DNA Controlled-Release Stent in Porcine Coronary Arteries," *Nature Biotechnology* 18:1181-1184, (Nov. 2000).

Kohilas, K. et al. "Effect of Prosthetic Titanium Wear Debris on Mitogen-Induced Monocyte and Lymphoid Activation," *J. Biomed Mater Res.* 47:95-103, (Apr. 1999).

Kwok, Connie et al. "Design of Infection-Resistant Antibiotic-Releasing Polymers: I. Fabrication and Formulation," *Journal of Controlled Release* 62 (1999), pp. 289-299.

Laboratory of Liposome Research. "Liposomes: General Properties," downloaded from the Internet on Feb. 9, 2006 at: http://www.unizh.ch/onkwww/lipos.htm, 5 pages.

Laham, R.J., "Intrapericardial Delivery of Fibroblast Growth Factor-2 Induces Neovascularization in a Porcine Model of Chronic Myocardial Ischemia," *J. Pharmacol Exper Therap* 292(2):795-802, (2000).

Leor, J. et al. "Bioengineered Cardiac Grafts—A New Approach to Repair the Infarcted Myocardium?" *Circulation* (2000); 102[suppl III] III-56-III-61.

Leor, J. et al. Gene Transfer and Cell Transplant: An Experimental Approach to Repair a 'Broken Heart', *Cardiovascular Research* 35 (1997), pp. 431-441.

Leroux, J.C. et al. "An Investigation on the Role of Plasma and Serum Opsonins on the Internalization of Biodegradable poly(D,L-lactic acid) Nanoparticles by Human Monocytes," *Life Sci.* 57(7):695-703 (1995), Abstract downloaded from the Internet at: http://www.ncbi.nlm.nih.gov/entrez/query.fcgi?cmd=Retrieve&db=pubmed, 1 page.

Lewin, Benjamin. "Repressor is Controlled by a Small Molecule Inducer", *Genes VII*, Oxford University Press, 7th ed., pp. 277-280, (2000).

Li, J. et al. "PR39, A Peptide Regulator of Angiogenesis," *Nature Medicine* 6(1):49-55, (Jan. 2000).

Li, W.W. et al. "Lessons to be Learned from Clinical Trials of Angiogenesis Modulators in Ischemic Diseases," Chapter 33, in Rubanyi, G. (ed). *Angiogenesis in Health & Disease: Basic Mechanisms and Clinical Applications*, Marcel Dekker, Inc. New York (2000).

Li, Y.Y. et al. "Differential Expression of Tissue Inhibitors of Metalloproteinases in the Failing Human Heart," *Circulation* 98(17):1728-1734, (1998).

Lindsey, M. et al. "Selective Matrix Metalloproteinase Inhibition Reduces Left Ventricular Remodeling but does not Inhibit Angiogenesis after Myocardial Infarction," *Circulation* 105(6):753-758, (2002).

Long, D.M.et al. "Self-Cleaving Catalytic RNA," *FASEB Journal*, 7:25-30, (1993).

Lopez, J. J. et al. "Angiogenic Potential of Perivascularly Delivered aFGF in a Porcine Model of Chronic Myocardial Ischemia," *Am. J. Physiol.* 274 (*Heart Circ. Physiol.* 43):H930-H936, (1998).

Lopez, J. J. et al. "VEGF Administration in Chronic Myocardial Ischemia in Pigs," *Cardiovasc Res.* 40(2):272-281 (1998), Abstract downloaded from the Internet at: http://www.ncbi.nlm.nih.gov/entrez/query.fcgi?cmd=Retrieve&db=pubmed, 1 page.

Lu, L. et al. "Biodegradable Polymer Scaffolds for Cartilage Tissue Engineering," in *Clinical Orthopaedics and Related Research*, Carl T. Brighton (ed.). No. 391S, pp. S251-270, (2001).

Luo, Y. et al. "Cross-linked Hyaluronic Acid Hydrogel Films: New Biomaterials for Drug Delivery," *Journal of Controlled Release*, 69:169-184, (2000).

Lyman, M.D. et al. "Characterization of the Formation of Interfacially Photopolymerized Thin Hydrogels in Contact with Arterial Tissue," *Biomaterials*, 17(3):359-64, (1996).

Mansour, S. et al. "Disruption of the proto-oncogene *int*-2 in mouse embryo-derived stem cells: a general strategy for targeting mutations to non-selectable genes," *Nature*, 336:348-352, (1988).

Martin, S.L. et al. "Total Synthesis and Expression in *Escherichia coli* of a Gene Encoding Human Tropoelastin," *Gene* (1995), Abstract, 1 page.

McDevitt, T. et al. "In vitro Generation of Differentiated Cardiac Myofibers on Micropatterned Laminin Surfaces," *J. Biomed Mater Res.* 60:472-479, (2002).

Narmoneva, D.A. et al. "Self-assembling short oligopeptides and the promotion of angiogenesis," *Biomaterials* 26 (2005) 4837-4846.

Nguyen, Kytai T. et al. "Photopolymerizable Hydrogels for Tissue Engineering Applications," *Biomaterials* 23:4307-4314, (2002).

Nikolic, S.D. et al. "New Angiogenic Implant Therapy Improves Function of the Ischemic Left Venticle," supplement to *Circulation. Abstracts From Scientific Sessions 2000*, 102(18):II-689, Abstract 3331 (Oct. 2000).

Nitinol Technical Information, "NiTi Smart Sheets," downloaded from the Internet on Dec. 10, 2002 at: http://www.sma-inc.com/information.html, 1 page.

Ohyanagi, H. et al. "Kinetic Studies of Oxygen and Carbon Dioxide Transport into or from Perfluorochemical Particles," *Proc. ISAO vol. 1* (*Artificial Organs vol. 2* (Suppl.)), pp. 90-92 (1977).

Ozbas, B. et al. "Salt-Triggered Peptide Folding and Consequent Self-Assembly into Hydrogels with Tunable Modulus," *Macromolecules* 37(19):7331-7337, (2004).

Ozbas-Turan, Suna. "Controlled Release of Interleukin-2 from Chitosan Microspheres," *Journal of Pharmaceutical Sciences* 91(5):1245-1251, (May 2002).

Palmiter R. et al. "Germ-Line Transformation of Mice," *Ann. Rev. Genet.* 20:465-499, (1986).

Patrick, C.R. "Mixing and Solution Properties of Organofluorine Compounds," Chapter 10, in Preparation, Properties and Industrial Applications of Organofluorine Compounds, R.E. Banks (ed.), 1st edition, pp. 323-342, Ellis-Horwood Ltd., Chichester:England (1982).

PCT Invitation to Pay Additional Fees for International Appln No. PCT/US03/18360, mailed Nov. 4, 2003 (3 pgs).

PCT International Search Report for International Appln No. PCT/US03/18360, mailed Jan. 28, 2004 (7 pgs).

PCT International Search Report for International Appln. No. PCT/US03/30464, mailed Feb. 9, 2004 (5 pages).

PCT International Preliminary Report on Patentability for International Appln. No. PCT/US2004/011356, mailed Nov. 3, 2005 (6 pgs).

PCT International Search Report and Written Opinion for International Appln No. PCT/US2005/045627, mailed Oct. 13, 2006 (15 pgs).

Peattie, R.A. et al. "Stimulation of In Vivo Angiogenesis by Cytokine-Loaded Hyaluronic Acid Hydrogel Implants," *Biomaterials* (Jun. 2004) 25(14), Abstract downloaded from: www.sciencedirect.com, 2 pages.

Penta, K. et al. "Dell Induces Integrin Signaling and Angiogenesis by Ligation of αVβ3," *J. Biolog. Chem.* 274(16):11101-11109, (Apr. 1999).

Perin, E.C. et al. "Transendocardial, Autologous Bone Marrow Cell Transplantation for Severe, Chronic, Ischemic Heart Failure," *Circulation* (2003), 1 page.

Pouzet, B. et al. "Is Skeletal Myoblast Transplantation Clinically Relevant in the Era of Angiotensin-Converting Enzyme Inhibitors?" *Circulation* 104[suppl I]:I-223-I-228, (Sep. 2001).

Prather et al. "Nuclear Transplantation in Early Pig Embryos," *Biol. Reprod.* 41:414-418, (1989).

ProSci Incorporated, "ILPIP (CT) Peptide," 1 page, May 2007.

Quellec, P. et al. "Protein Encapsulation Within Polyethylene Glycol-coated Nanospheres. I. Physicochemical Characterization," *J. Biomed. Mater. Res.* 42(1), (1998) Abstract, 1 page.

Ramirez-Solis, R. et al. "Gene Targeting in Embryonic Stem Cells," *Methods in Enzymology*, 225:855-878, (1993).

Rowley, J. et al. "Alginate Hydrogels as Synthetic Extracellular Matrix Materials," *Biomaterials* 20:45-53, (1999).

Sawhney, A.S. et al. "Bioerodible Hydrogels Based on Photopolymerized Poly(ethylene glycol)-co-poly(a-hydroxy acid) Diacrylate Macromers," *Macromolecules* 26(4):581-587, (1993).

Sbaa-Ketata, E. et al. "Hyaluronan-Derived Oligosaccharides Enhance SDF-1-Dependent Chemotactic Effect on Peripheral Blood Hematopoietic CD34+ Cells," *Stem Cells* (2002), 20(6):585-587, "Letter to the Editor" downloaded from the Internet at: http://stemcells.alphamedpress.org/cgi/content/full/20/6/585, 5 pages.

Segura, T. et al. "[216c]-DNA Delivery From Hyaluronic Acid/Collagen Hydrogels," AIchE Technical Program Paper Detail, *American Institute of Chemical Engineers* (ALCHE Annual Meeting 2003), Abstract downloaded from the Internet at: http://www.aiche.org/cofnerences/techprogram/paperdetail.asp?PaperID=1465&DSN=annual, 2 pages.

Segura, T. et al. "Crosslinked Hyaluronic Acid Hydrogels: A Strategy to Functionalize and Pattern," *Biomaterials* 26:359-371, (2005).

Segura, T. et al. "Substrate-Mediated DNA Delivery: Role of the Cationic Polymer Structure and Extent of Modification," *Journal of Controlled Release* 93:69-84, (2003).

Segura, T. et al. "Surface-Tethered DNA Complexes for Enhanced Gene Delivery," *Bioconjugate Chem* 13(3):621-629, (2002).

Shibasaki, F. et al. "Suppression of Signalling Through Transcription Factor NF-AT by Interactions Between Calcineurin and Bcl-2," *Nature* (1997) 386(6626), Abstract downloaded from the Internet at: http://www.ncbi.nlm.nih.gov/entrez/query.fcgi?CMD=Text &DB=pubmed, 1 page.

Shin, H. et al. "Attachment, Proliferation, and Migration of Marrow Stromal Osteoblasts Cultured on Biomimetic Hydrogels Modified with an Osteopontin-Derived Peptide," *Biomaterials* 25:895-906, (2004).

Shin, H. et al. "In Vivo Bone & Soft Tissue Response to Injectable, Biodegradable oligo(poly(ethylene glycol) fumerate) Hydrogels," *Biomaterials* 24:3201-3211, (Mar. 2003).

Shu, et al. "Disulfide-crosslinked hyaluronan-gelatin hydrogel films: a covalent mimic of the extracellular matrix for in vitro cell growth," *Biomaterials* (Sep. 2003) 24(21)3825-3834, Abstract downloaded from the Internet at: http://www.sciencedirect.com, 1 page.

Simons, M. et al. "Clinical Trials in Coronary Angiogenesis: Issues, Problems, Consensus—An Expert Panel Summary," *Circulation* 102:e73-e86, (Sep. 2000), pp. 1-14.

Spenlehauer, G. et al. "In vitro and in vivo Degradation of poly (D,L lactide/glycolide) Type Microspheres Made by Solvent Evaporation Method," *Biomaterials* 10:557-563, (Oct. 1989).

Spinale, Francis G. "Matrix Metalloproteinases—Regulation and Dysregulation in the Failing Heart," *Circ. Res.* 90:520-530, (2002).

Springer, M. et al. "Angiogenesis Monitored by Perfusion with a Space-Filling Microbead Suspension," *Mol. Ther.* (2000) 1(1):82-87, Abstract downloaded from the Internet at: http://www.ncbi.nlm.nih.gov/entrez/query.fcgi?cmd=Retrieve&db=PubMed, 1 page.

Storm, G. et al. "Surface Modification of Nanoparticles to Oppose Uptake by the Mononuclear Phagocyte System," *Advanced Drug Delivery Reviews* (Oct. 1995), 17(1):31-48, Abstract downloaded from the Internet at: http://www.sciencedirect.com, 1 page.

Strauer, B. et al. "Repair of Infarcted Myocardium by Autologous Intracoronary Mononuclear Bone Marrow Cell Transplantation in Humans," *Circulation* 106:1913-1918, (2002).

Tybulewicz, V. et al. "Neonatal lethality and lymphopenia in mice with a homozygous disruption of the c-*abl* proto-oncogene," *Cell* (Jun. 1991), 65(7):1153-1163, Abstract downloaded from the Internet at: http://www.sciencedirect.com, 2 pages.

Unger, E.F. et al. "Effects of a Single Intracoronary Injection of Basic Fibroblast Growth Factor in Stable angina Pectoris" *Am. J. Cardiol* 85(12):1414-1419 (Jun. 2000), Abstract downloaded from the Internet at: http://www.sciencedirect.com, 2 pages.

van der Giessen, W.J. et al. "Marked Inflammatory Sequelae to Implantation of Biodegradable and Nonbiodegradable Polymers in Porcine Coronary Arteries," *Circulation* 94(7):1690-1697 (Oct. 1996).

van Luyn, M.J.A. et al. "Cardiac Tissue Engineering: Characteristics of in Unison Contracting Two-and Three-Dimensional Neonatal Rat Ventricle Cell (Co)-Cultures," *Biomaterials* 23:4793-4801, (2002).

Vercruysse, K.P. et al. "Synthesis and in Vitro Degradation of New Polyvalent Hydrazide Cross-Linked Hydrogels of Hyaluronic Acid," *Bioconjugate Chem* 8(5):686-694 (1997), Abstract downloaded from the Internet at: http://pubs.acs.org/cgi-bin/abstract.cgi/bcches/1997/8/i05/abs/bc9701095.html, 1 page.

Visscher, G.E. et al. "Tissue Response to Biodegradable Injectable Microcapsules," *Journal of Biomaterials Applications* 2 (Jul. 1987), pp. 118-119.

Vlodaysky, I. et al. "Extracellular Matrix-resident Basic Fibroblast Growth Factor: Implication for the Control of Angiogenesis," *J. Cell Biochem*, 45(2):167-176 (Feb. 1991), Abstract downloaded from the Internet at: http://www.ncbi.nlm.nih.gov/entrez/query.fcgi?cmd=Retrieve&db=PubMed, 1 page.

Wasielewski, S. "Ischämische Erkrankungen, Gefäbneubildung anregen" *Deutsche Apotheker Zeitung* (Jan. 2000), 140(3):232-233, Stuttgart (DE).

Witzenbichler, B., et al. "Vascular Endothelial Growth Factor-C (VEGF-C/VEGF-2) Promotes Angiogenesis in the Setting of Tissue Ischemia" *AM Pathol.* 153(2):381-394, (Aug. 1998).

Yamamoto, N. et al. "Histologic Evidence that Basic Fibroblast Growth Factor Enhances the Angiogenic Effects of Transmyocardial Laser Revascularization," *Basic Res. Cardiol.* 95(1):55-63, (Feb. 2000).

Zervas, L. et al. "On Cysteine and Cystine Peptides. II. S-Acylcysteines in Peptide Synthesis," *J. Am. Chem. Soc.* 85(9):1337-1341, (May 1963).

Zheng, W. et al. "Mechanisms of coronary angiogenesis in response to stretch: role of VEGF and TGF-beta," *Am J Physiol Heart Circ Physiol.* 280(2):H909-H917, (Feb. 2001).

Zimmermann, W. et al. "Engineered Heart Tissue for Regeneration of Diseased Hearts," Biomaterials 25:1639-1647, (2004).

\* cited by examiner

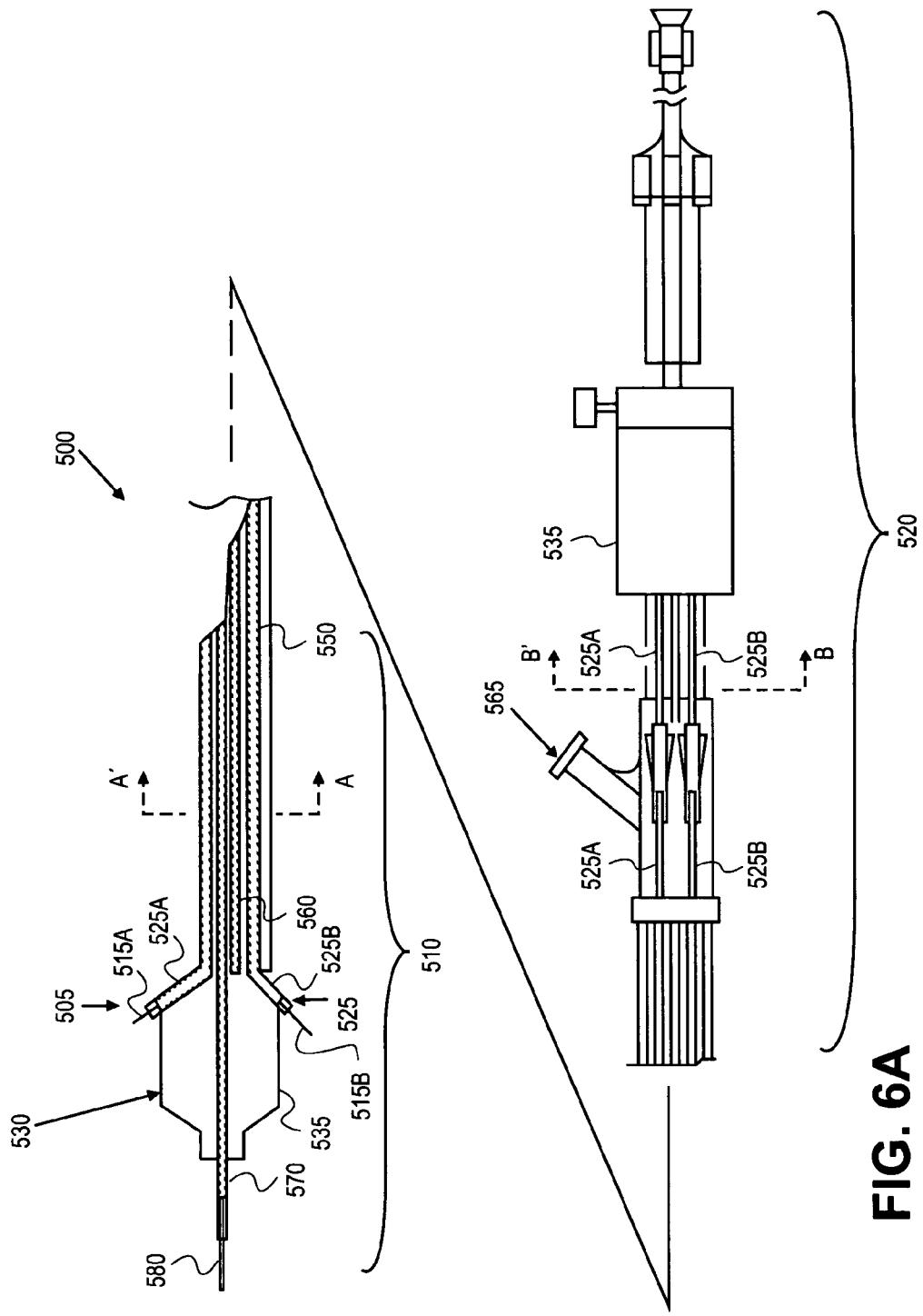

METHODS AND COMPOSITIONS FOR TREATING POST-MYOCARDIAL INFARCTION DAMAGE

CROSS REFERENCE TO RELATED APPLICATIONS

This is a continuation-in-part of application Ser. No. 11/361,920, filed Feb. 23, 2006, which is a continuation-in-part of application Ser. No. 11/110,223, filed Apr. 19, 2005, now pending.

FIELD OF INVENTION

Post-myocardial infarction treatments and compositions.

BACKGROUND OF INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that often results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arties. An example of a mechanical procedure includes balloon angioplasty with stenting, while an example of a therapeutic agent application includes the administration of a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infracted region and the healthy tissue resulting in uneven stress and strain distribution in the left ventricle. Once an MI occurs, remodeling of the heart begins. The principle components of the remodeling event include myocyte death, edema and inflammation, followed by fibroblast infiltration and collagen deposition, and finally scar formation. The principle component of the scar is collagen. Since mature myocytes of an adult are not regenerated, the infarct region experiences significant thinning. Myocyte loss is the major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

SUMMARY OF INVENTION

Methods and compositions for treating post-myocardial infarction damage are herein disclosed. In some embodiments, a carrier may be loaded with a treatment agent. The carrier can be formulated from a bioerodable, sustained-release substance. The resultant loaded carrier may then be suspended in one component of a two-component matrix for simultaneous delivery to a post-myocardial infarction treatment area.

BRIEF DESCRIPTION OF DRAWINGS

FIGS. 6A-6C illustrate an alternative embodiment of a dual-needle injection device which can be used to deliver the compositions of the present invention.

DETAILED DESCRIPTION

Methods and compositions for treating post-myocardial infarction damage are herein disclosed. In some embodiments, a carrier with a treatment agent may be fabricated. The carrier can be formulated from a bioerodable, sustained-release substance. The resultant loaded carrier may then be suspended in at least one component of a two-component matrix system for simultaneous delivery to a post-myocardial infarction treatment area.

Figure 1:
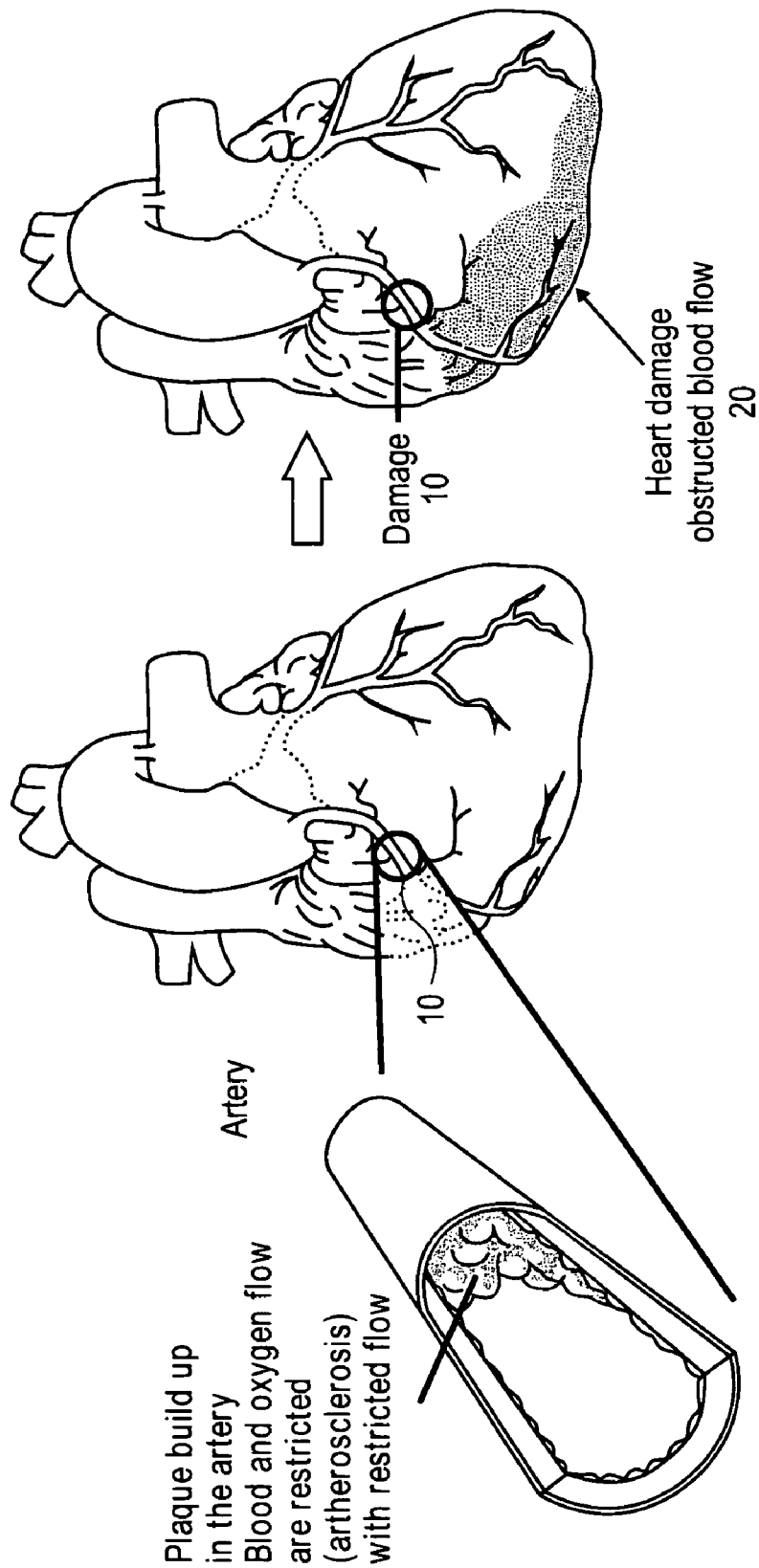
FIGS. 1A-1B illustrate the progression of heart damage once the build-up of plaque in an artery induces an infarct to occur.

FIGS. 1A-1B illustrate the progression of heart damage once the build-up of plaque induces an infarct to occur. FIG. 1A illustrates a site 10 where blockage and restricted blood flow can occur from, for example, a thrombus or embolus. FIG. 1B illustrates resultant damage area 20 to the left ventricle that can result from the lack of oxygen and nutrient flow carried by the blood to the inferior region left of the heart. The damage area 20 will likely undergo remodeling, and eventually scarring, resulting in a non-functional area.

Treatment Agents

Treatment agents to treat post-myocardial infarction treatment areas may include: (i) agents that promote angiogenesis (angiogenesis promoting factors); (ii) agents that promote cell survival (cell survival promoting factors); and (iii) agents that recruit endogenous progenitor and/or stem cells (endogenous recruiting factors). Various forms of treatment agents are intended to include, but are not intended to be limited to, drugs, biologically active agents, chemically active agents, therapeutic agents, and the like, and pharmaceutical compositions thereof, which can be used in the delivery of a treatment agent to a treatment site as described herein.

"Angiogenesis" is the promotion or causation of the formation of new blood vessels. After an MI, the infarct tissue as well as the border zone and the remote zone around the infarct tissue begin to remodel. Scar tissue forms in the infarct region as the granulation is replaced with collagen. Stress from blood pressure cause the scar to thin out and stretch. The perfusion in this region is typically 10% of the healthy zone, decreasing the number of active capillaries. Increasing the number of capillaries may lead to an increase in compliance of the ventricle due to filling up with blood. Other benefits of increasing blood flow to the infarcted region include providing a route for circulating stem cells to seed and proliferate in the infarct region. Angiogenesis may also lead to increased oxygenation for the surviving cellular islets within the infarct region, or to prime the infarct region for subsequent cell transplantation for myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen and therefore function to full capacity are also compromised; thus, angiogenesis would be beneficial in these regions as well.

In some embodiments, angiogenesis promoting factors include, but are not intended to be limited to, growth factors such as isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (I1-8), hematopoietic growth factors, erythropoietin, granulocyte-colony stimulating factors (G-CSF) and platelet-derived endothelial growth factor (PD-ECGF). In some embodiments, angiogenesis promoting factors include, but are not intended to be limited to, peptides, such as PR39, PR11 and angiogenin, small molecules, such as PHD inhibitors, or other agents, such as eNOS enhancers.

Endogenous cardiomyocyte (myocytes) apoptosis is the major etiological factor of wall thinning and chamber dilation and may ultimately lead to progression of cardiac myopathy. After an infarction, mature myocytes of an adult are not regenerated which can lead to significant thinning in the infarct region. Thus, factors which promote cell survival applied to the infarct region are believed to be beneficial. In some embodiments, cell survival promoting factors include, but are not intended to be limited to, growth factors such as insulin-like growth factor (IGF-1) and human growth factor (HGF), which are known to mediate cell growth, differentiation and survival of a variety of cell types. In addition, small molecules such as, for example, HMG-CoA reductase inhibitors (statins) and capsase inhibitors can also promote cell survival and inhibit apoptosis.

To assist in the generation of new cells at the infarct region, autologous or allogeneic stem cells may be delivered to a patient. "Autologous" means the donor and recipient of the stem cells are the same. "Allogeneic" means the donor and recipient of the stem cells are different. Cell survival promoting factors can also be used to increase the survivability of autologous and allogeneic implanted stem cells at the infarct region.

Cardiac progenitor cells are highly specialized stem cells which have shown the ability to differentiate into certain types of fully mature cardiac tissue. Examples of cardiac progenitor cells include, but are not limited to, c-Kit(+), Sca-1(+) and Isl-1(+). Thus, factors which recruit endogenous factors when applied to the infarct region are believed to be beneficial. In some embodiments, an endogenous recruiting factor can include, for example, HGF. HGF has been shown to control cell motility and promote cell migration. If applied post-infarction, HGF can assist in mobilizing and recruiting resident cardiac progenitor cells to the infarct region. In some embodiments, an endogenous recruiting factor can include, but is not intended to be limited to, stromal cell-derived factor 1 (SDF-1). SDF-1 is the ligand for the CXCR4 receptor, which is a surface receptor on circulating endothelial progenitor cells. Thus, when applied in or around the infarct region, SDF-1 may facilitate the homing of circulating endothelial progenitor cells to induce neovascularization.

It is contemplated that any of the above-described treatment agents can be used singularly or in combination thereof. In addition, other treatment agents, including but not limited to, anti-inflamrnatory, anti-platelet, anti-coagulant, anti-fibrin, anti-thrombotic, anti-mitotic, anti-biotic, anti-allergic, anti-oxidant, anti-proliferative, or anti-migratory agents, may be optionally used singularly or in combination thereof.

Sustained-Release Carriers

Bioerodable carriers (hereinafter interchangeably referred to as sustained-release carriers) infused with (or without) a treatment agent can be used for the sustained or controlled release of treatment agent for maximum benefit to the infarct region. It is believed that a large percentage of treatment agent delivered directly to the infarct region, or even diffused within a gel-like matrix, will be substantially washed away by the body's natural mechanisms, thus lessening the benefit of the treatment agent that may otherwise be obtained. Thus, sustained-release carriers infused with treatment agent that release the treatment agent over an extended time period can be beneficial by increasing the amount of time in which the infarct region is exposed to the treatment agent. Sustained-release carriers include, but are not limited to, (i) microparticles or nanoparticles (hereinafter interchangeably referred to as microparticles), (ii) microfibers or nanofibers (hereinafter interchangeably referred to as microfibers) and (iii) liposomes and polymerosomes.

In addition, in some embodiments, a bioerodable carrier may be infused with (or without) a treatment agent and delivered to a treatment site to act as a "docking site" for endogenous myocardial stem cells and encourage their differentiation into cardiomyocytes.

A.

In some embodiments, the sustained-release carrier is a microparticle. Various methods can be employed to formulate and infuse or load the microparticles with treatment agent. In some embodiments, the microparticles are prepared by a water/oil/water (W/O/W) double emulsion method. In the WI phase, an aqueous phase containing treatment agent, is dispersed into the oil phase consisting of polymer dissolved in organic solvent (e.g., dichloromethane) using a high-speed homogenizer. Examples of sustained-release polymers include, but are not limited to, poly(D,L-lactide-co-glycolide) (PLGA), poly(D,L-lactide) (PLA) or PLA-PEEP co-polymers, poly-ester-amide co-polymers (PEA) and polyphophazines. The primary water-in-oil (W/O) emulsion is then dispersed to an aqueous solution containing a polymeric surfactant, e.g., poly(vinyl alcohol) (PVA), and further homogenized to produce a W/O/W emulsion. After stirring for several hours, the microparticles are collected by filtration.

B.

In some embodiments, the sustained-release carrier is a microfiber or nanofiber. For example, the treatment agent (or no treatment agent) infused microfiber can be formulated by electrospinning. "Electrospinning" is a process by which microfibers are formed by using an electric field to draw a polymer solution from the tip of a capillary to a collector. A voltage is applied to the polymer solution which causes a stream of solution to be drawn toward a grounded collector. Electrospinning generates a web of fibers which can be subsequently processed into smaller lengths.

Examples of sustained-release polymers which can be used in electrospinning include, but are not limited to, PLGA, PLA or PLA-PEEP co-polymers, PEA, polyphosphazines and collagen. In one method, the treatment agent is mixed with a bioerodable polymer solution, a solvent and a surfactant. Examples of surfactants can include, but are not limited to, anionic or cationic surfactants. Useful anionic surfactants include, but are not intended to be limited to, bis(2-ethylhexyl) sodium sulfosuccinate (AOT), bis (2-ethylhexyl) phosphate (NaDEHP), tauroglycocholate, and sodium lauryl sulfate. A useful cationic surfactant is tetradecyltrimethylammonium bromide (TTAB). An example of a solvent includes, but is not limited to, hexafluoro isopropanol. The treatment agent-infused polymer solution is then subjected to electrospinning. As the solvent evaporates during electrospinning, the treatment agent incorporates and distributes within the polymer by non-covalent interactions. The resultant microfibers which can be from about 0.5 µm to about 3 µm in diameter form a web which may then be processed into smaller lengths of about 0.5 µm to about 500 µm. Based on the treatment agent, in some applications, microfibers may be a preferred sustained-release carrier due to the non-aqueous process by which they are formed. In some applications, microspheres may be preferable when the treatment agent is hydrophilic. In some applications, a microfiber is a preferred sustained-release carrier due to its release pharmacokinetic profile when compared to the release pharmacokinetic profile of a microsphere. In some cases, microspheres as well as microfibers can be used as a carrier of one or more than one treatment agent as the two types of carriers will provide different pharmacokinetic release profiles which may be advantageous for therapy.

In one embodiment, fibers can be electrospun from collagen and elastin dissolved in 1,1,1,3,3,3-hexafluoro-2-propanol (HFP), forming a polymer solution. A treatment agent can be added to the polymer solution. A surfactant and a stabilizer can be used to evenly disperse the treatment agent in the solvent. The polymer solution can then be loaded into a syringe and placed in a syringe pump for metered dispensing at a predetermined rate. A positive output lead of a high voltage supply can be attached to a needle on the syringe. The needle can be directed to a stainless steel grounded target placed approximately 10 cm from the needle tip, which can be rotated at a predetermined speed to ensure an even coating. The distance of the needle from the target can be varied depending upon the diameter of the fibers needed. The resultant microfibers are from about 0.5 µm to about 3 µm in diameter and the resulting non-woven mat of fibers can then be processed into smaller lengths of about 0.5 µm to about 500 µm.

C.

In some embodiments, the sustained-release carrier is a liposome or a polymerosome. "Liposomes" are artificial vesicles that are approximately spherical in shape and can be produced from natural phospholipids and cholesterol. In one method, phospholipids are mixed with cholesterol in chloroform. Suitable phospholipids include, but are not limited to, dimyristoyl phosphatidyl choline or dipalmitoyl ethanolamine. In some embodiments, hydrophobic treatment agent can be added with an optional co-solvent, such as heptane or toluene. The liposomes may also be hydrophilically modified with an agent such as polyethylene glycol or dextran. After mixing, the solvent (and optional co-solvent) can be evaporated with heat or ambient temperature in a round bottom flask. Resultant lipids will be deposited on the glass surface. In some embodiments, hydrophilic treatment agent and water can be added to the flask and sonicated to form liposomes. The resultant suspension can be pressure filtered through ceramic pore size controlled filters to reduce liposome particle size. In the case of a polymerosome, a similar manufacturing technique can be used as that of a liposome. Polymerosomes can be formed from di-block co-polymers of differing solubility. For example, one block can be hydrophobic, e.g., poly lactic acid, polycaprolactone, n-butyl acrylate, and the other block can be hydrophilic, e.g., poly (ethylene glycol), poly(acrylic acid).

Matrix Systems

A biocompatible matrix system can be used to suspend the treatment agent or the treatment agent-infused sustained-release carrier for delivery to the infarct region. In some embodiments, the matrix system can be a one-component or a two-component gel. In some embodiments, the matrix system is a two-component gel. Two-component gels can include, for example, fibrin glues (e.g., two components comprising fibrinogen and thrombin), self-assembled peptides or alginate constructs.

In some embodiments, the matrix system is a one-component gel. An example of a one-component gel includes an acrylate agent that is biocompatible. The one-component gel serves in one aspect to disperse the sustained-release carrier in order to form a more uniform scaffold over the entire infarct zone and may include border zone as well. For example, the one-component gel may be sodium hyaluronate. The gel disperses the sustained-release carrier acting as a suspending media.

A.

In some applications, the two-component gelation system includes a fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevent fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the infarct region. Fibrin glue can undergo gelation at about 10 to about 60 seconds. Examples of other fibrin glue-like systems include, but are not limited to, Tisseel™ (Baxter), CoSeal™ (Baxter), Crosseal™ (Omrix Biopharmaceuticals, Ltd.), Hemaseel® (Haemacure Corp.) and CoStasis® (Angiotech Pharmaceuticals).

B.

In some embodiments, the two-component gel comprises self-assembled peptides. Self-assembled peptides generally include repeat sequences of alternating hydrophobic and hydrophilic amino acid chains. The hydrophilic amino acids are generally charge-bearing and can be anionic, cationic or both. Examples of cationic amino acids are lysine and arginine. Examples of anionic amino acids are aspartic acid and glutamic acid. Examples of hydrophobic amino acids are alanine, valine, leucine, isoleucine or phenylalanine. Self-assembled peptides can range from 8 to about 40 amino acids in length and can assemble into nanoscale fibers under conditions of physiological pH and osmolarity. In sufficient concentration and over time, the fibers can assemble into an interconnected structure that appears macroscopically as a gel. Self-assembled peptides typically undergo gelation between several minutes to several hours. Examples of self-assembled peptides include, but are not limited to: AcN-RARADADARARADADA-CNH$_2$ (RAD 16-II) wherein R is arginine, A is alanine, D is aspartic acid, and Ac indicates acetylation, sequence RARADADARARADADA may be referred to herein as SEQ ID NO: 1; VKVKVKVKV-PP-TKVKVKVKV-NH$_2$ (MAX-1) wherein V is valine, K is lysine and P is proline, sequence VKVKVKVKV-PP-TKVKVKVKV may be referred to herein as SEQ ID NO: 2; and AcN-AEAEAKAKAEAEAKAK-CNH$_2$ wherein A is alanine, K is lysine and E is glutamic acid (EAK16-II), sequence AEAEAKAKAEAEAKAK may be referred to herein as SEQ ID NO: 3.

EXAMPLE

In one example, the self-assembled peptide is RAD 16-II. At low pH and osmolarity, RAD 16-II forms a solution. At physiological pH and osmolarity, RAD 16-II forms a gel although gel formation can be slow. In some embodiments, RAD 16-II is mixed with phosphate buffer saline (PBS) to form a first component solution. In some embodiments, the first component solution can be co-injected with a second component comprising sodium chloride, sucrose or other osmolarity modifying substance using, for example, a dual-injection delivery assembly. In some embodiments, the components can be co-injected with carriers such as angiogenesis promoting factors, cell survival promoting factors and/or endogenous recruiting factors. These factors bind non-specifically to the self-assembled peptides by electrostatic interactions, and this binding can control or retard the release of the factors.

C.

In some embodiments, the two-component gel is an alginate construct. For example, the alginate construct may be collagen or gelatin grafted alginate. In one example, a first component can be a solution of about 0.5 percent to about 1.0 percent alginate while a second component can be a solution of about 40 mM to about 180 mM calcium chloride. One example of a suitable amount of components is about 200 microliters of alginate solution and about 200 microliters of calcium chloride. In one embodiment, a desired amount of a treatment agent may be introduced with the alginate solution.

Methods of Manufacture

Figure 2:
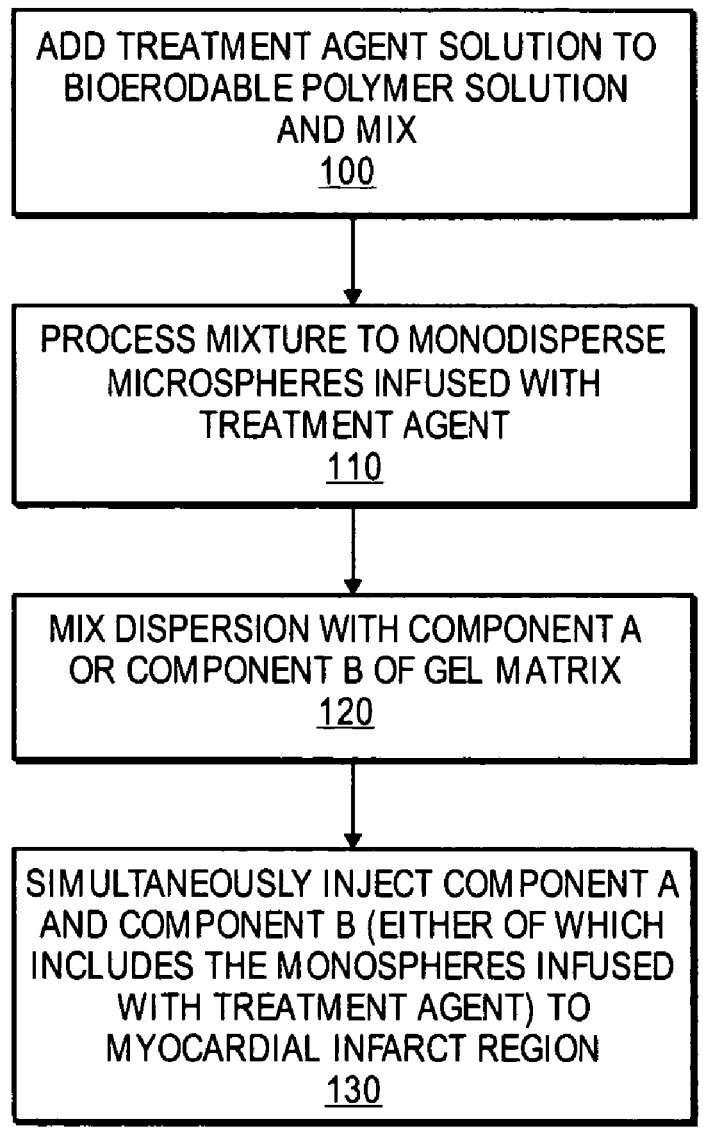
FIG. 2 schematically represents a method for preparing a two-component gel matrix with a sustained carrier loaded with treatment agent interdispersed therein.

FIG. 2 schematically represents a method for preparing a two-component gel matrix with a sustained carrier loaded with treatment agent interdispersed therein. A treatment agent, such as an angiogenesis promoting factor, cell survival promoting factor, endogenous recruiting factor or any combination thereof can be added to a bioerodable polymer such as PLGA or PEA and PLA-PEEP co-polymers or polyphosphazenes (100). In some embodiments, a W/O/W process can be used. The mixture can be processed to monodisperse the resultant treatment agent loaded microspheres (110). The microspheres can be in a range from about 5 μm to about 200 μm, preferably from about 10 μm to about 50 μm. Next, the resultant dispersion can be added to one component of a two-component gel such as fibrin glue (120). In one embodiment, the two-component gel includes component A and component B, wherein component A is fibrinogen and component B is thrombin. Component A and component B can then be separately but simultaneously injected into the myocardial infarct region by a dual-injection delivery assembly for treatment thereof (130).

Figure 3:
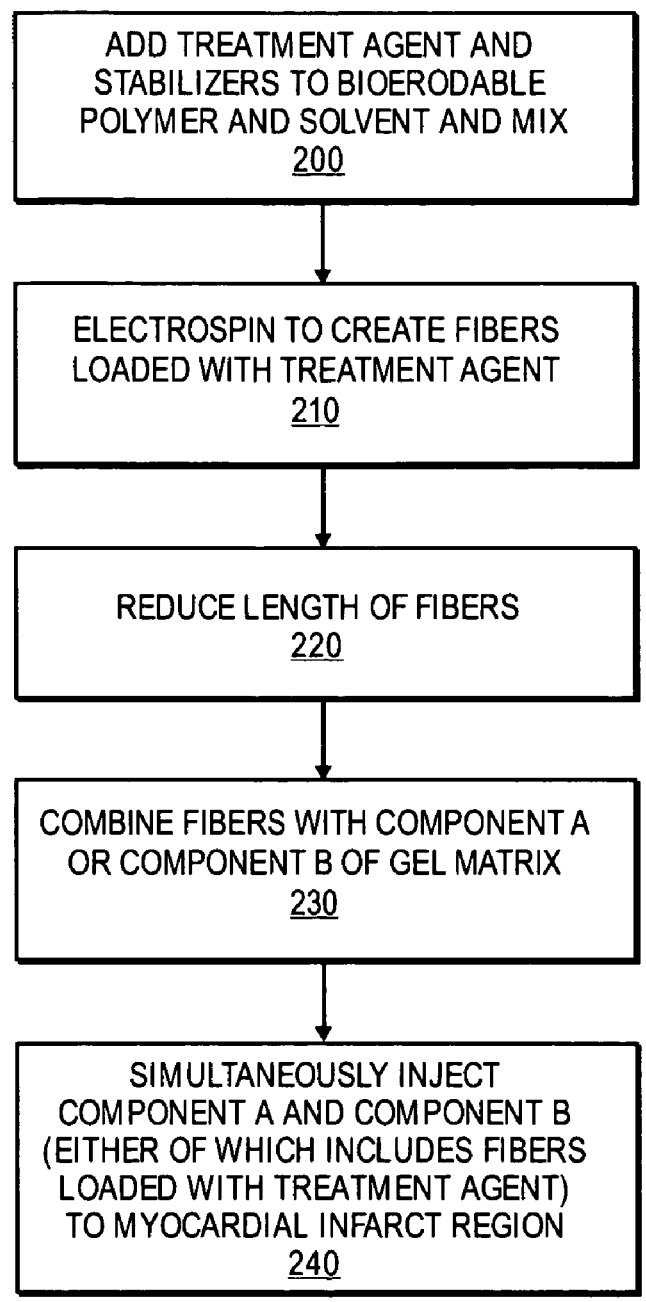
FIG. 3 schematically represents an alternative method for preparing a two-component gel matrix with a sustained carrier loaded with treatment agent interdispersed therein.

FIG. 3 schematically represents an alternative method for preparing a two-component gel matrix with a sustained carrier loaded with treatment agent interdispersed therein. A treatment agent, such as an angiogenesis promoting factor, cell survival promoting factor, endogenous recruiting factor or any combination thereof can be added to a bioerodable polymer such as PLGA or PEA and PLA-PEEP co-polymers or polyphosphazenes or collagen (200) with solvent. For collagen/elastin electrospun fibers, a suitable solvent can be HFP. In some embodiments, an aqueous system may be used. The mixture can then be subjected to electrospinning to create interwoven fibers (210) with a diameter in a range from about 0.2 μm to about 3 μm. The fibers may then be processed into smaller of length from about 0.5 μm to about 500 μm (220). The fibers may be processed by cryogenic grinding, subjected to ultrasound in water, or subjected to ultrasound in a volatile solvent that is a non-solvent for both the polymer and the encapsulated protein or other agent or subjected to any other suitable method to reduce their size. Next, the resultant fibers can be added to one component of a two-component gel such as fibrin glue (230). In one embodiment, the two-component gel includes component A and component B, wherein component A is fibrinogen and component B is thrombin. Component A and component B can then be separately but simultaneously injected into the myocardial infarct region by a dual-injection delivery assembly for treatment thereof (240).

Figure 4:
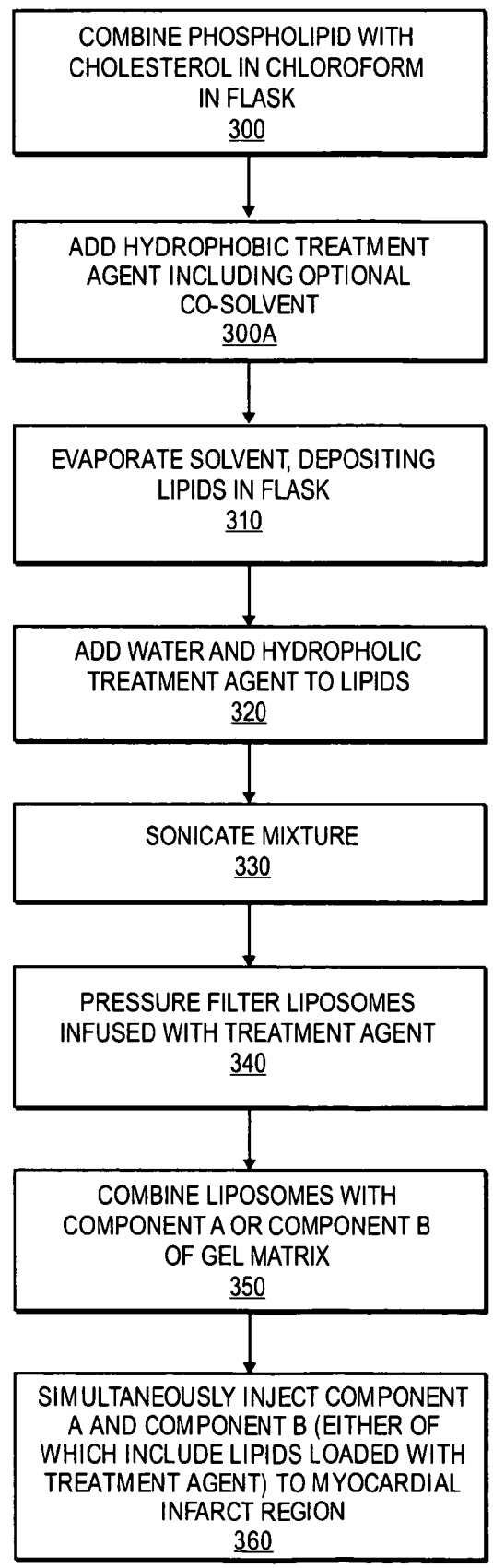
FIG. 4 schematically represents a second alternative method for preparing a two-component gel matrix with a sustained carrier loaded with treatment agent interdispersed therein.

FIG. 4 schematically represents another alternative method for preparing a two-component gel matrix with a sustained carrier loaded with treatment agent interdispersed therein. A phospholipid substance can be combined with cholesterol in a solvent such as chloroform (300) in a round bottom flask. In some embodiments, a hydrophobic treatment agent including an optional co-solvent can be added thereto (300A). The solvent(s) can be evaporated depositing lipids on the glass surface (310). Next, water is added and in some embodiments, a hydrophilic treatment agent (320). Then, the mixture is sonicated to form liposomes (330) and optionally pressure-filtered to reduce liposome particle size (340). Next, the resultant liposomes can be added to one component of a two-component gel such as fibrin glue (350). In one embodiment, the two-component gel includes component A and component B, wherein component A is fibrinogen and component B is thrombin. Component A and component B can then be separately but simultaneously injected into the myocardial infarct region by a dual-injection delivery assembly for treatment thereof (360).

EXAMPLE

In one embodiment, collagen electrospun fibers can be processed to a range from about 200 nm and about 1300 nm. The range of electrospun fibers is approximately the range of naturally occurring type 1 and type 3 fibers which make up the heart matrix. Thus, the electrospun fibers may mimic endogenous fibers and accelerate growth of repair tissue to the infarct region, in particular, on the heart. The fibers can be dispersed throughout one component of a two-component gel. The two components can then be delivered to myocardial infarct region. The fibers can provide "docking sites" for endogenous myocardial stem cells and encourage their differentiation into cardiomyocytes. The gel can provide temporary containment of the fibers and prevent premature removal by macrophage cells.

The fibers can be fabricated such that they include an agent or no agent. Examples of agents can include a chemoattractant, such as SDF-1, or a cell survival promoting factor, such as IGF-1. In one embodiment, SDF-1 may be incorporated within the electrospun fibers and the resultant agent infused electrospun fibers may be dispersed throughout one component of a two-component gel. When delivered, the release of SDF-1 may recruit endogenous stem cells to the infarct region where they will adhere to the electrospun fibers and differentiate into stem cells.

In another embodiment, IGF-1 may be incorporated within the electrospun fibers and the resultant agent infused electrospun fibers may be dispersed throughout one component of a two-component gel. Stem cells may be incorporated within the other component of the two-component gel. When delivered, the stem cells may be temporally immobilized in the gel and adhere to the electrospun fibers. IGF-1 may enhance stem cell survival.

It should be appreciated that any of the above-described methods may be combined to treat an infarct region.

Methods of Treatment

Devices which can be used to deliver each component of the gel include, but are not limited to, dual-needle left-ventricle injection devices and dual-needle transvascular wall injection. Methods of access to use the injection devices include access via the femoral artery or the sub-xiphoid. "Xiphoid" or "xiphoid process" is a pointed cartilage attached to the lower end of the breastbone or sternum, the smallest and lowest division of the sternum. Both methods are known by those skilled in the art.

Figure 5A:
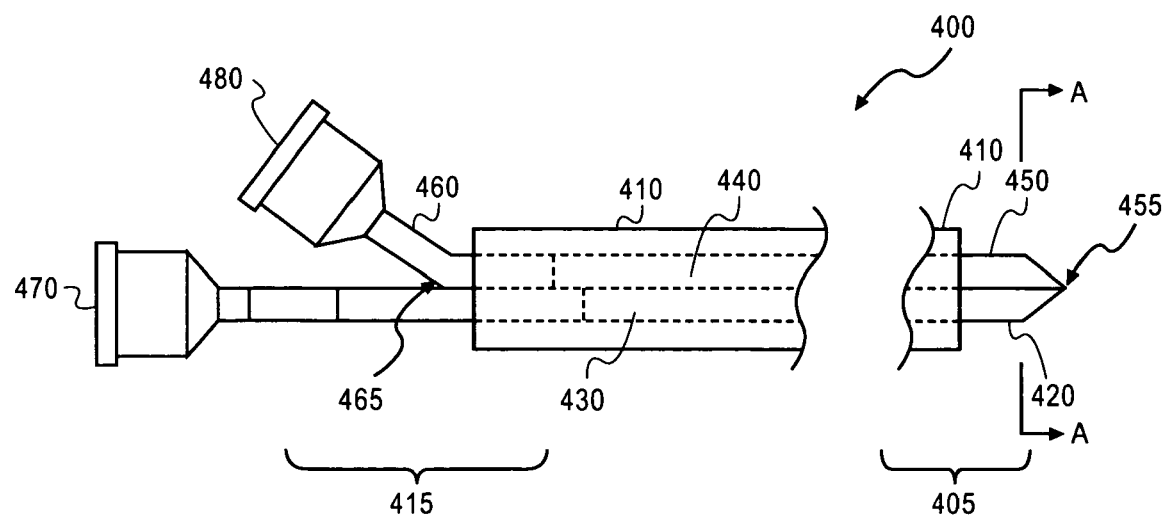
FIGS. 5A-5B illustrate an embodiment of a dual-needle injection device which can be used to deliver the compositions of the present invention.
Figure 5B:
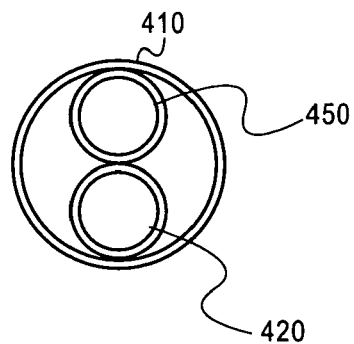

FIGS. 5A-5B illustrate an embodiment of a dual-needle injection device which can be used to deliver the compositions of the present invention. Delivery assembly 400 includes lumen 410 which may house delivery lumens, guidewire lumens and/or other lumens. Lumen 410, in this example, extends between distal portion 405 and proximal end 415 of delivery assembly 400.

In one embodiment, delivery assembly 400 includes main needle 420 disposed within delivery lumen 430. Main needle 420 is movably disposed within delivery lumen 430. Main needle 420 is, for example, a stainless steel hypotube that extends a length of the delivery assembly. Main needle 420 includes a lumen with an inside diameter of, for example, 0.08 inches (0.20 centimeters). In one example for a retractable needle catheter, main needle 420 has a needle length on the order of 40 inches (1.6 meters) from distal portion 405 to proximal portion 415. Lumen 410 also includes separate, possibly smaller diameter, auxiliary lumen 440 extending, in this example, co-linearly along the length of the catheter (from a distal portion 405 to proximal portion 415). Auxiliary lumen 440 is, for example, a polymer tubing of a suitable material (e.g., polyamides, polyolefins, polyurethanes, etc.). At distal portion 405, auxiliary lumen 440 is terminated to auxiliary needle end 450 co-linearly aligned with a delivery end of needle 420. Auxiliary lumen 440 may be terminated to auxiliary needle end 450 with a radiation-curable adhesive, such as an ultraviolet curable adhesive. Auxiliary needle end 450 is, for example, a stainless steel hypotube that is joined co-linearly to the end of main needle 420 by, for example, solder (illustrated as joint 455). Auxiliary needle end 450 has a length on the order of about 0.08 inches (0.20 centimeters). FIG. 5B shows a cross-sectional front view through line A-A' of delivery assembly 400. FIG. 5B shows main needle 420 and auxiliary needle 450 in a co-linear alignment.

Referring to FIG. 5A, at proximal portion 415, auxiliary lumen 440 is terminated to auxiliary side arm 460. Auxiliary side arm 460 includes a portion extending co-linearly with main needle 420. Auxiliary side arm 460 is, for example, a stainless steel hypotube material that may be soldered to main needle 420 (illustrated as joint 465). Auxiliary side arm 460 has a co-linear length on the order of about, in one example, 1.2 inches (3 centimeters).

The proximal end of main needle 420 includes adaptor 470 for accommodating a substance delivery device (e.g., a component of a two-component bioerodable gel material). Adaptor 470 is, for example, a molded female luer housing. Similarly, a proximal end of auxiliary side arm 460 includes adaptor 480 to accommodate a substance delivery device (e.g., a female luer housing).

The design configuration described above with respect to FIGS. 5A-5B is suitable for introducing two-component gel compositions of the present invention. For example, a gel may be formed by a combination (mixing, contact, etc.) of a first component and a second component. Representatively, a first component may be introduced by a one cubic centimeters syringe at adaptor 470 through main needle 420. At the same time or shortly before or after, second component including treatment agent loaded sustained-release particles may be introduced with a one cubic centimeter syringe at adaptor 480. When the first and second components combine at the exit of delivery assembly 400 (at an infarct region), the materials combine (mix, contact) to form a bioerodable gel.

Figure 6B:
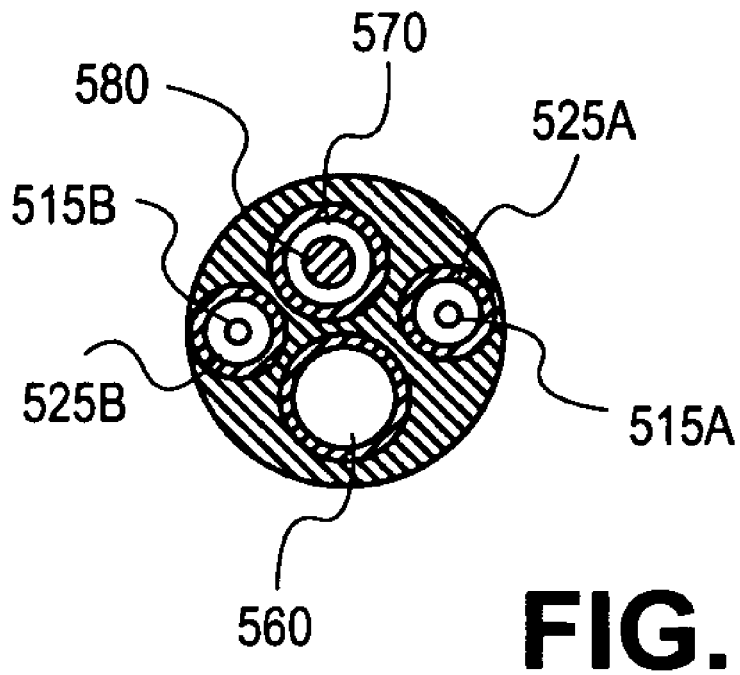
Figure 6C:
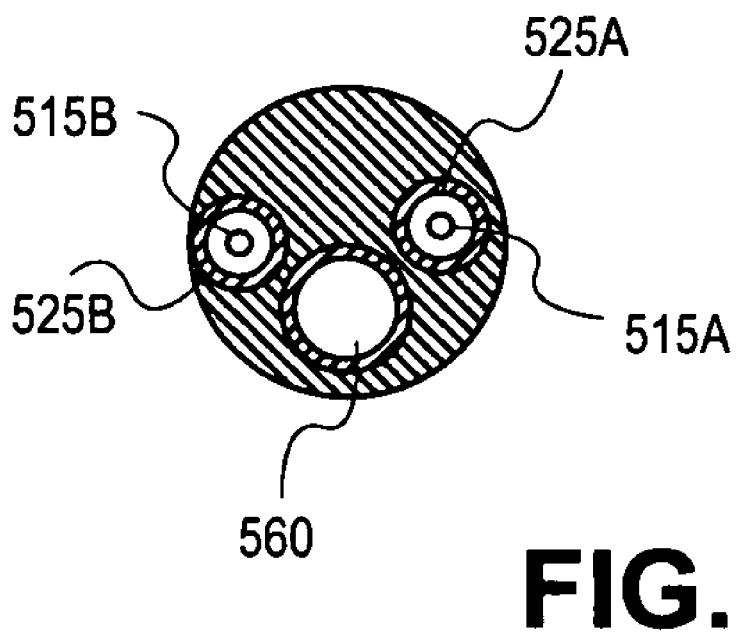

FIGS. 6A-6C illustrate an alternative embodiment of a dual-needle injection device which can be used to deliver two-component gel compositions of the present invention. In general, the catheter assembly 500 provides a system for delivering substances, such as two-component gel compositions, to or through a desired area of a blood vessel (a physiological lumen) or tissue in order to treat a myocardial infarct region. The catheter assembly 500 is similar to the catheter assembly 500 described in commonly-owned, U.S. patent application Ser. No. 6,554,801, titled "Directional Needle Injection Drug Delivery Device", and incorporated herein by reference.

In one embodiment, catheter assembly 500 is defined by elongated catheter body 550 having proximal portion 520 and distal portion 510. FIG. 6B shows catheter assembly 500 through line A-A' of FIG. 6A (at distal portion 510). FIG. 6C shows catheter assembly 500 through line B-B' of FIG. 6A.

Guidewire cannula 570 is formed within catheter body (from proximal portion 510 to distal portion 520) for allowing catheter assembly 500 to be fed and maneuvered over guidewire 580. Balloon 530 is incorporated at distal portion 510 of catheter assembly 500 and is in fluid communication with inflation cannula 560 of catheter assembly 500.

Balloon 530 can be formed from balloon wall or membrane 335 which is selectively inflatable to dilate from a collapsed configuration to a desired and controlled expanded configuration. Balloon 530 can be selectively dilated (inflated) by supplying a fluid into inflation cannula 560 at a predetermined rate of pressure through inflation port 565. Balloon wall 335 is selectively deflatable, after inflation, to return to the collapsed configuration or a deflated profile. Balloon 530 may be dilated (inflated) by the introduction of a liquid into inflation cannula 560. Liquids containing treatment and/or diagnostic agents may also be used to inflate balloon 530. In one embodiment, balloon 530 may be made of a material that is permeable to such treatment and/or diagnostic liquids. To inflate balloon 530, the fluid can be supplied into inflation cannula 560 at a predetermined pressure, for example, between about one and 20 atmospheres. The specific pressure depends on various factors, such as the thickness of balloon wall 335, the material from which balloon wall 335 is made, the type of substance employed and the flow-rate that is desired.

Catheter assembly 500 also includes substance delivery assembly 505 for injecting a substance into a myocardial infarct region. In one embodiment, substance delivery assembly 505 includes needle 515*a* movably disposed within hollow delivery lumen 525*a*. Delivery assembly 505 includes needle 515*b* movably disposed within hollow delivery lumen 525*b*. Delivery lumen 525*a* and delivery lumen 525*b* each extend between distal portion 510 and proximal portion 520. Delivery lumen 525*a* and delivery lumen 525*b* can be made from any suitable material, such as polymers and copolymers of polyamides, polyolefins, polyurethanes and the like. Access to the proximal end of delivery lumen 525*a* or delivery lumen 525*b* for insertion of needle 515*a* or 515*b*, respectively is provided through hub 535. Delivery lumens 525*a* and 525*b* may be used to deliver first and second components of a two-component gel composition to a myocardial infarct region.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What claimed is:

1. A composition comprising:
    a bioerodable material comprising a first component and a second component;
    a bioerodable carrier dispersed throughout one of the first component or the second component, the bioerodable carrier comprising a microfiber having a length of 0.5 µm to 500 µm; and
    a treatment agent disposed within the bioerodable carrier.

2. The composition of claim 1, wherein the material is a two-component gel selected from the group consisting of an alginate construct system, a fibrin glue system and a self-assembled peptide system.

3. The composition of claim 2, wherein the two-component gel is an alginate construct system comprising collagen grafted alginate as the first component and calcium chloride as the second component.

4. The composition of claim 2, wherein the two-component gel is a self-assembled peptide system comprising one of SEQ ID NO: 1, SEQ ID NO: 2 or SEQ ID NO: 3 as the first component and one of sucrose or sodium chloride as the second component.

5. The composition of claim 2, wherein the two-component gel is a fibrin glue system comprising fibrinogen or a derivative thereof as the first component and thrombin as the second component.

---

SEQUENCE LISTING

```
<160> NUMBER OF SEQ ID NOS: 3

<210> SEQ ID NO 1
<211> LENGTH: 16
<212> TYPE: PRT
<213> ORGANISM: Unknown
<220> FEATURE:
<223> OTHER INFORMATION: Self-assembled peptide

<400> SEQUENCE: 1

Arg Ala Arg Ala Asp Ala Asp Ala Arg Ala Arg Ala Asp Ala Asp Ala
1               5                   10                  15

<210> SEQ ID NO 2
<211> LENGTH: 20
<212> TYPE: PRT
<213> ORGANISM: Unknown
<220> FEATURE:
<223> OTHER INFORMATION: Self-assembled peptide

<400> SEQUENCE: 2

Val Lys Val Lys Val Lys Val Lys Val Pro Pro Thr Lys Val Lys Val
1               5                   10                  15

Lys Val Lys Val
            20

<210> SEQ ID NO 3
<211> LENGTH: 16
<212> TYPE: PRT
<213> ORGANISM: Unknown
<220> FEATURE:
<223> OTHER INFORMATION: Self-assembled peptide

<400> SEQUENCE: 3

Ala Glu Ala Glu Ala Lys Ala Lys Ala Glu Ala Glu Ala Lys Ala Lys
1               5                   10                  15
```

6. The composition of claim 1, wherein the microfiber of the bioerodable carrier is a first carrier, and the bioerodable carrier further comprises a second carrier selected from the group consisting of bioerodable polymers and liposomes.

7. The composition of claim 6, wherein the second carrier is a particle.

8. The composition of claim 7, wherein the particle is one of a microsphere, a nanosphere or a polymerosome.

9. The composition of claim 7, wherein the particle is an electrospun nanofiber.

10. The composition of claim 1, wherein the treatment agent is selected from the group consisting of an angiogenesis promoting factor, a cell survival promoting factor and an endogenous recruiting factor.

11. The composition of claim 10, wherein the angiogenesis promoting factor is selected from the group consisting of vasoendothelial growth factor, fibroblast growth factor, Del 1, hypoxia inducing factor, monocyte chemoattractant protein, nicotine, platelet derived growth factor, insulin-like growth factor 1, transforming growth factor, hepatocyte growth factor, estrogens, follistatin, proliferin, prostaglandin E1, prostaglandin E2, tumor necrosis factor, Interleukin 8, hematopoietic growth factors, erythropoietin, granulocyte-colony stimulating factors, platelet-derived endothelial growth factor, PR39, PR11, angiogenin, a PHD inhibitor, and a eNOS enhancer.

12. The composition of claim 10, wherein the cell survival promoting factor is selected from the group consisting of insulin-like growth factor, a human growth factor, a HMG-CoA reductase inhibitor and a capsase inhibitor.

13. The composition of claim 10, wherein the endogenous recruiting factor is one of human growth factor or stromal cell-derived factor 1.

* * * * *